United States Patent
Liu

(10) Patent No.: US 10,292,787 B2
(45) Date of Patent: May 21, 2019

(54) SURGICAL INSTRUMENT WITH RFID TAG ADHERED THERETO WITH FIRST AND SECOND ADHESIVES WHERE THE FIRST AND SECOND ADHESIVES ARE DIFFERENT TYPES OF ADHESIVES

(71) Applicant: XERAFY SINGAPORE PTE. LTD., Singapore (SG)

(72) Inventor: Zhijia Liu, Shanghai (CN)

(73) Assignee: XERAFY SINGAPORE PTE. LTD., Singapore (SG)

( * ) Notice: Subject to any disclaimer, the term of this patent is extended or adjusted under 35 U.S.C. 154(b) by 0 days.

(21) Appl. No.: 15/977,559

(22) Filed: May 11, 2018

(65) Prior Publication Data
US 2018/0256286 A1    Sep. 13, 2018

Related U.S. Application Data

(63) Continuation of application No. PCT/CN2016/105479, filed on Nov. 11, 2016.

(30) Foreign Application Priority Data

Nov. 13, 2015    (CN) .......................... 2015 1 0781224

(51) Int. Cl.
*G08B 21/00* (2006.01)
*A61B 90/90* (2016.01)
(Continued)

(52) U.S. Cl.
CPC .......... *A61B 90/90* (2016.02); *G06K 19/0723* (2013.01); *G06K 19/07749* (2013.01);
(Continued)

(58) Field of Classification Search
CPC ........................... G06K 19/0723; A61B 90/90
(Continued)

(56) References Cited

U.S. PATENT DOCUMENTS

2002/0030609 A1    3/2002   Baumgartner
2008/0238631 A1*   10/2008  Blake ..................... A61B 90/90
                                                     340/10.51
(Continued)

FOREIGN PATENT DOCUMENTS

CN    1617317       5/2005
CN    101051358     10/2007
(Continued)

OTHER PUBLICATIONS

Garg et al., "Detection and Removal of Rain from Videos", Proceedings of the 2004 IEEE Computer Society Conference on Computer Vision and Pattern Recognition (CVPR04), Jun. 27-Jul. 2, 2004, pp. 528-535.
(Continued)

*Primary Examiner* — Mark S Rushing
(74) *Attorney, Agent, or Firm* — McDonnell Boehnen Hulbert & Berghoff LLP

(57) ABSTRACT

A surgical instrument and a method for installing a RFID label on the surgical instrument are provided. The surgical instrument includes a surgical instrument body, a RFID label and an adhesive, the surgical instrument body and the RFID label are fixedly connection by the adhesive, the adhesive comprises a first adhesive and a second adhesive; the first adhesive is disposed between a bottom surface of the RFID label and a surface of the surgical instrument body, the other surfaces of the RFID label are covered by the second adhesive, the second adhesive also covers an intersection of the RFID label with the surgical instrument body; and the first adhesive and the second adhesive are different types of adhesives, and an adhesive intensity of the first adhesive is greater than an adhesive intensity of the second adhesive, and fluidity of the second adhesive is greater than fluidity of the first adhesive.

11 Claims, 5 Drawing Sheets

(51) Int. Cl.
*G06K 19/07* (2006.01)
*G06K 19/077* (2006.01)
*A61B 50/00* (2016.01)
*A61B 17/00* (2006.01)
*G06K 17/00* (2006.01)

(52) U.S. Cl.
CPC .............. *G06K 19/07758* (2013.01); *A61B 2017/00526* (2013.01); *A61B 2017/00951* (2013.01); *A61B 2050/002* (2016.02); *G06K 2017/009* (2013.01)

(58) Field of Classification Search
USPC .................................................. 340/539.12
See application file for complete search history.

(56) References Cited

U.S. PATENT DOCUMENTS

| | | | | |
|---|---|---|---|---|
| 2015/0061834 | A1* | 3/2015 | Khoury | A61B 5/065 340/10.1 |
| 2015/0138030 | A1* | 5/2015 | Yosui | H01Q 1/38 343/895 |
| 2016/0296299 | A1* | 10/2016 | Mortensen | B29C 65/02 |

FOREIGN PATENT DOCUMENTS

| | | |
|---|---|---|
| CN | 102129597 | 7/2011 |
| CN | 102989631 | 3/2013 |
| CN | 103020696 | 4/2013 |
| CN | 203108733 | 8/2013 |
| CN | 104778493 | 7/2015 |
| CN | 104837431 | 8/2015 |
| EP | 1120 824 | 2/2004 |
| EP | 2109065 | 10/2009 |
| WO | 2011/054355 | 5/2011 |

OTHER PUBLICATIONS

Jha et al., "Entropy-Based Rain Detection and Removal", 2013 International Conference on Control, Automation, Robotics and Embedded Systems (CARE), Dec. 16, 2013, pp. 1-4.

Ma et al., "Video Image Clarity Algorithm Research of USV Visual System under the Sea Fog", Advances in Swarm Intelligence, Springer Berlin Heidelberg, Berlin, Jun. 12, 2013, pp. 436-444.

Supplementary Partial European Search Report prepared by the European Patent Office in application No. EP 15 82 8078, dated Feb. 28, 2018.

Official Action issued by the Chinese Patent Office in application No. 201510781224.5, dated Aug. 10, 2018.

* cited by examiner

SURGICAL INSTRUMENT WITH RFID TAG ADHERED THERETO WITH FIRST AND SECOND ADHESIVES WHERE THE FIRST AND SECOND ADHESIVES ARE DIFFERENT TYPES OF ADHESIVES

TECHNICAL FIELD

The present disclosure relates to a surgical instrument, particularly relating to an installing way of a tracking and positioning structure of the surgical instrument.

BACKGROUND

At present, in medical accidents, many accidents are caused by the imperfect disinfection of surgical instruments and loss of instruments in patients. Traceability of the medical instruments as usually mentioned refers to tracking source of raw materials and components of medical instruments, processing, sales, and use of the products. Due to traceability, production, sale and use of each specific implantable and interventional medical instrument may be tracked, a condition of the patient using the medical instrument, and thereby causing adverse reaction may be clarified.

On the other hand, with rapid development of a radio frequency identification (RFID) technology, more and more RFID application requirements have been put forward. With deeper application of RFID, a further challenge is proposed for the medical filed, i.e., tracking surgical instruments to avoid serious medical accidents and complications as a result of the surgical instruments being left in patients.

Due to limitations of miniaturization and integration of the current RFID tag, installing a RFID tag on surgical instruments has become considerable difficulty and challenge. The current RFID tag is mainly composed of a RFID chip, a tag antenna and a package material. The RFID tag, when being used, is mainly installed on the surface of the surgical instrument or tool, so as to track and management of the tool and the surgical instrument. Existing RFID tag is attached to surgical instrument generally by the way of welding.

SUMMARY

Regarding to the problems existed in the prior art, an object of an embodiment of the present disclosure is to provide an installing method, by which the RFID tag can be attached to the surface of the instrument firmly without affecting actual use of the instrument.

To achieve the above-mentioned object, a part of embodiments of the present disclosure provide technical solutions as follows:

One aspect of the present disclosure provides a surgical instrument, including a surgical instrument body, a RFID tag and an adhesive, the surgical instrument body and the RFID tag are fixedly connection as a whole by the adhesive, wherein the adhesive comprises a first adhesive and a second adhesive; the first adhesive is disposed between a bottom surface of the RFID tag and a surface of the surgical instrument body, the other surfaces of the RFID tag are covered by the second adhesive, the second adhesive also covers an intersection of the RFID tag with the surgical instrument body; and the first adhesive and the second adhesive are different types of adhesives, and an adhesive intensity of the first adhesive is greater than an adhesive intensity of the second adhesive, and fluidity of the second adhesive is greater than fluidity of the first adhesive.

In another embodiment of the present disclosure, a groove is disposed on the surgical instrument body, the RFID tag and a face of the adhesive in contact with the surgical instrument body are within the groove.

In another embodiment of the present disclosure, a groove is disposed on the surgical instrument body, a size of an opening of the groove is matched with a size of the bottom of the RFID tag, and the RFID tag is engaged in the groove.

In another embodiment of the present disclosure, the first adhesive is selected from any one of a silane adhesive and an organic silicone adhesive; and the second adhesive is an epoxy adhesive.

In another embodiment of the present disclosure, a portion of the surgical instrument body adhered to the bottom surface of the RFID tag is a rough surface.

In another embodiment of the present disclosure, a portion of the bottom surface of the RFID tag adhered to the surgical instrument body is a rough surface.

In another embodiment of the present disclosure, the first adhesive is a conductive adhesive.

In another embodiment of the present disclosure, the surgical instrument further includes a first metal layer disposed between the surgical instrument body and the bottom surface of the RFID tag, the first metal layer is adhered to the surgical instrument body by a third adhesive, and the first metal layer is further adhered to the bottom surface of the RFID tag by a fourth adhesive.

In another embodiment of the present disclosure, a material of the third adhesive is identical to a material of the first adhesive.

In another embodiment of the present disclosure, the surgical instrument further includes a second metal layer disposed on a top of the RFID tag, the second metal layer is adhered to the top of the RFID tag by a fourth adhesive, and the second adhesive covers the second metal layer and the RFID tag.

In another embodiment of the present disclosure, a material of the fourth adhesive is identical to the material of the first adhesive.

One aspect of the present disclosure provides a method for installing a RFID tag on a surgical instrument, comprising following steps of:

A. cleaning a surface of the surgical instrument body;
B. coating the first adhesive on the surface of the surgical instrument body;
C. placing the RFID tag on the first adhesive;
D. curing for a first time;
E. coating the second adhesive on the RFID tag and the surface of the surgical instrument body adjacent to the RFID tag;
F. curing for a second time.

In another embodiment of the present disclosure, in the steps B and E, an adhesive applying device employs an air compressor and a pneumatic dispenser; the air compressor is connected with the pneumatic dispenser through an air tube; the pneumatic dispenser is connected to an adhesive syringe through a dispensing air outlet pipe; and the adhesive syringe has a needlestick with a diameter of 1 mm.

In another embodiment of the present disclosure, in the step D, curing for a first time needs a temperature in a range of 20-35° C., a humidity >30%, and the curing time more than or equal to 12 hours.

One aspect of the present disclosure provides a method for installing a RFID tag on a surgical instrument, comprising following steps of:

A. providing a surgical instrument body, on which surface treatment is performed;

B. cleaning the surface of the surgical instrument body;

C. providing the first adhesive, and coating the first adhesive on the treated surface of the surgical instrument body;

D. providing the RFID tag, and sticking the RFID tag to the first adhesive;

E. curing for a first time;

F. providing the second adhesive to be coated on the RFID tag and the surface of the surgical instrument body adjacent to the RFID tag;

G. curing for a second time.

In another embodiment of the present disclosure, in the step A, performing the surface treatment on the surgical instrument body is to arrange a groove, in which the groove has a size slightly larger than the RFID tag intended to be installed on the surgical instrument body;

in the step C, the first adhesive is coated on the bottom of the groove;

in the step F, the second adhesive is coated within the groove.

In another embodiment of the present disclosure, in the step A, performing the surface treatment on the surgical instrument body is to arrange a groove, in which the groove has an opening with a size that is matched with the size of the bottom of the RFID tag intended to be installed on the surgical instrument body;

in the step C, the first adhesive is coated on the bottom of the groove;

in the step D, the RFID tag is engaged in the groove while the RFID tag is adhered onto the first adhesive.

In another embodiment of the present disclosure, in the step A, performing the surface treatment on the surgical instrument body is roughing or shallow-trenching;

in the step C, coating the first adhesive at the rough or shallow trench.

One aspect of the present disclosure provides a method for installing a RFID on a surgical instrument, comprising following steps of:

A. providing a surgical instrument body, and cleaning the surface of the surgical instrument body;

B. providing a third adhesive, and coating the third adhesive on the surface of the surgical instrument body;

C. providing a first metal layer, and sticking the first metal layer onto the third adhesive;

D. curing for a first time;

E. providing a first adhesive, and coating the first adhesive on the first metal layer;

F. providing a RFID tag, and sticking the RFID tag to the first adhesive;

G. curing for a second time;

H. providing a fourth adhesive, and coating the fourth adhesive on the RFID tag;

I. providing a second metal layer, and sticking the second metal layer to the RFID tag;

J. curing for a third time;

K. providing a second adhesive, and coating the second adhesive on the RFID tag and the surface of the surgical instrument body adjacent to the RFID tag;

L. curing for a fourth time.

BRIEF DESCRIPTION OF THE DRAWINGS

The embodiments of the present disclosure will be interpreted in further detail with reference to the accompanying drawings.

DETAILED DESCRIPTION

Typical embodiments embodying features and advantages of this disclosure will be set forth in detail. It should be understood that various modifications may be made on different embodiments of this disclosure without departing from the scope of this disclosure, wherein the description and drawings in essential are used for description but not limit to this disclosure.

The First Embodiment

Figure 1:
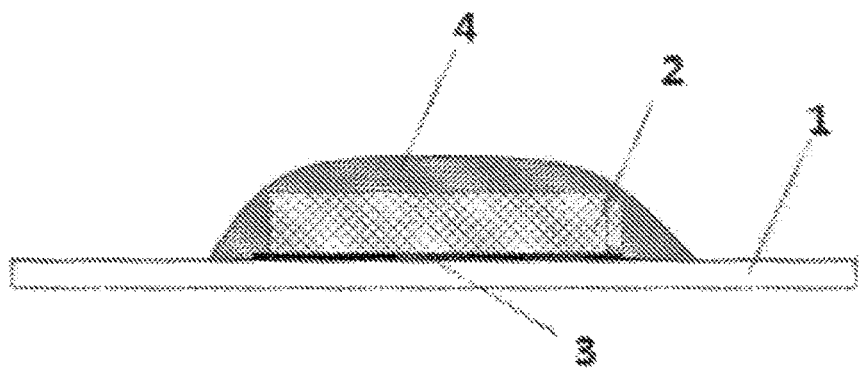
FIG. 1 is a schematic cross-sectional view of a RFID tag for a surgical instrument in an embodiment as provided by way of an example of the present disclosure.

As shown in FIG. 1, the first embodiment of the present disclosure provides a surgical instrument including a RFID tag 1 and a surgical instrument body 2. A first adhesive 3 is disposed between a bottom surface of the RFID tag 1 and a surface of the surgical instrument body 2. The other surfaces of the RFID tag 1 are covered by a second adhesive 4. The second adhesive 4 also covers an intersection of the periphery of the RFID tag 1 with the surgical instrument body 2. The first adhesive 3 and the second adhesive 4 are made of different materials. An adhesive intensity of the first adhesive 3 is greater than an adhesive intensity of the second adhesive 4, and fluidity of the second adhesive 4 is greater than fluidity of the first adhesive 3.

Function of the first adhesive 3 is mainly to stick and fix the RFID tag 1 and the surgical instrument body 2. The first adhesive 3 needs to have an extremely high adhesive intensity, so as to ensure that the RFID tag 1 cannot fall from the surgical instrument body 2 during use, cleaning and disinfection of the surgical instrument. Function of the second adhesive 4 is mainly to cover and protect the RFID tag 1, so when the second adhesive 4 is coated on the RFID tag 1, the second adhesive 4 needs to have a better flowability, which can cover the surface of the RFID tag 1 and a portion which connects the RFID tag 1 to the surgical instrument body 2 such that the RFID tag 1 is completely wrapped and protected. When the second adhesive 4 is cured, it is required that such material has a greater reliability and safety, which can resist high temperature and high pressure, to allow the material not to be damaged, to comply with medical safety standards and cannot produce toxic and harmful substances in the process of cleaning and disinfecting the surgical instruments. The first adhesive 3 may be selected from any one of a silane adhesive and an organic silicone adhesive. The second adhesive 4 is an epoxy adhesive. The silane adhesives or the organic silicone adhesives has a stronger adhesive intensity to satisfy the function of the first adhesive 3. The epoxy resin adhesive has a better flowability before curing and has a better reliability and safety after curing to be in line with the requirements of the second adhesive 4.

In the first embodiment of the present disclosure, different materials of the adhesive are respectively used for sticking the RFID tag 1 and the surgical instrument body 2, and covering and protecting the RFID tag 1, such that the RFID tag 1 can be firmly adhered to the surgical instrument body 2, and also has a greater reliability and safety, to be in line with the medical safety standards.

Referring to FIG. 1, in one implementation, the first adhesive 3 may be a conductive adhesive. When the first adhesive 3 is a conductive adhesive, corresponding to that a ground face of the RFID tag 1 is electrically connected to the surgical instrument body 2, to increase an area of the ground face of the RFID tag 1 and enhance directionality of the tag, such that a gain of the RFID tag is improved.

Figure 2:
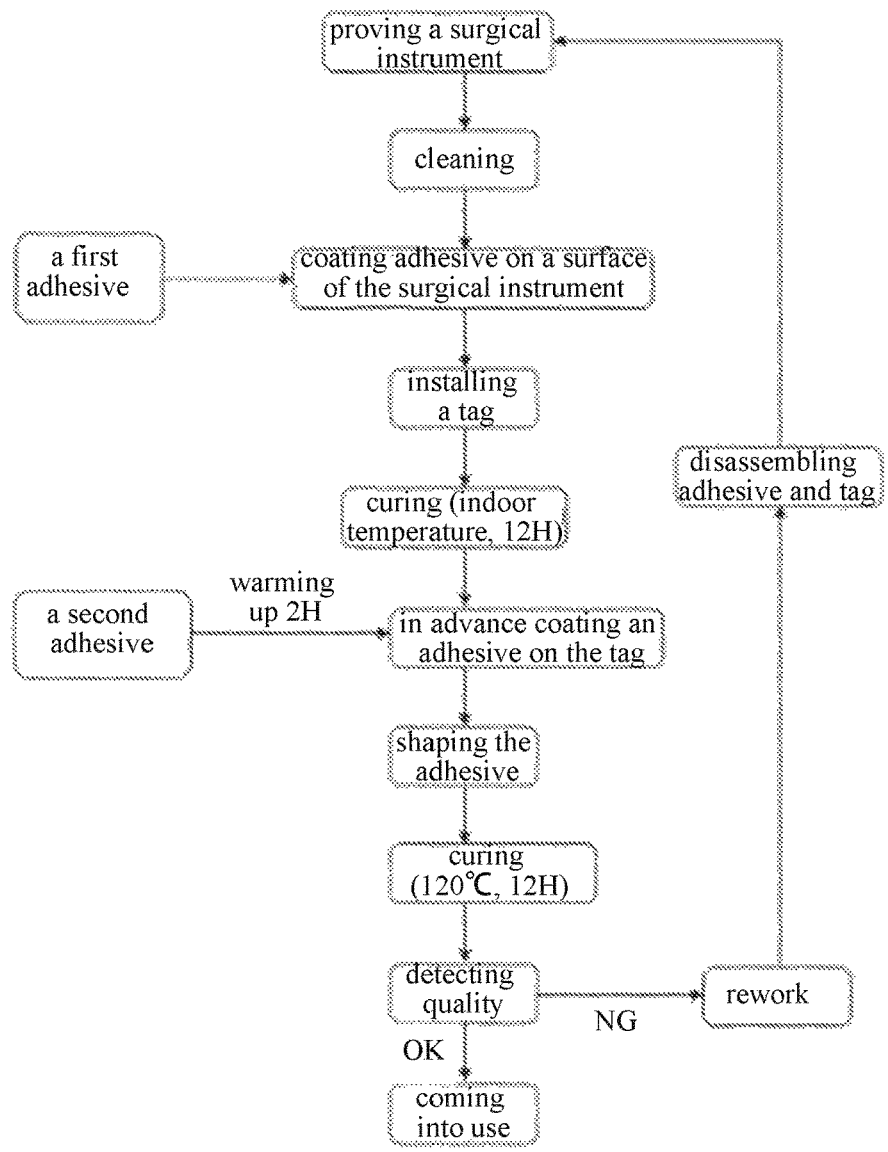
FIG. 2 is a schematic view of steps of installing the RFID tag for the surgical instrument in an embodiment as provided by way of an example of the present disclosure.

As shown in FIG. 2, the first embodiment of the present disclosure also provides a installing method of a RFID tag used in the surgical instrument. The installing method has specific steps as follows:

A. providing a surgical instrument body and cleaning the surface of the surgical instrument body;

B. applying the first adhesive on the surface of the surgical instrument body;

C. providing a RFID tag, and sticking the RFID tag on the first adhesive;

D. curing for the first time;

E. coating the second adhesive on the RFID tag and the surface of the surgical instrument body that is adjacent to the RFID tag;

F. curing for the second time.

In this embodiment, curing may be understood, for example, as a process of diverting the adhesive from low molecules to macromolecules. In this process, the RFID tag 1 and the surgical instrument body 2 in FIG. 1 of the aforesaid embodiment are bonded intensively and covered for protection by the first adhesive 3 and the second adhesive 4. In this embodiment, the curing for the first time in the step D may be understood, for example, as bonding the bottom of the RFID tag to the surgical instrument body, and the curing for the second time in the step F, that is, curing by baking, may be understood, for example, as covering and protecting the surface of the RFID tag by using the second adhesive 4.

The actual operation of the aforesaid steps will be described in detail in conjunction with FIG. 2 and FIG. 3.

Firstly, according to an appearance of the surgical instrument, a RFID tag suitable for being installed is selected, and according to the surface of the surgical instrument and size of the RFID tag selected to be installed, an appropriate installing position for the RFID tag is automatically determined. Referring to FIG. 3(*a*) and FIG. 3(*b*), in various embodiments, a strip-shaped RFID tag 1*a* or a circular RFID tag 1*b* may be selected according to the appearance of the surgical instrument body 2.

For example, the cleaning step may be performed before installing the tag. For example, a surface of the position of the instrument where the tag is installed is wiped by using alcohol of concentration ≥85%, so that there is no oil stains and/or foreign matters remained, and then, an operation of applying adhesive can be performed.

Figure 3A:
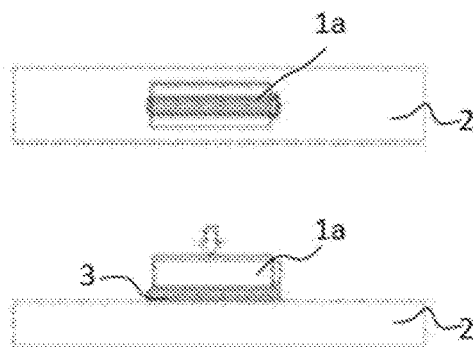
FIG. 3(a) and FIG. 3(b) are schematic views of a step C of installing the RFID tag for the surgical instrument in an embodiment as provided by way of an example of the present disclosure.
Figure 3B:
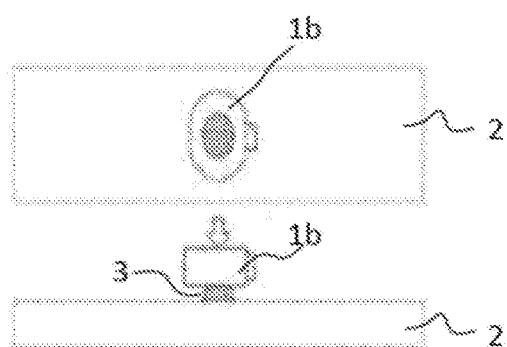

Referring to FIG. 3(*a*) and FIG. 3(*b*), the first adhesive 3 is coated on the surface of the surgical instrument body 2. The first adhesive 3 needs to be coated with an appropriate size, shape, and amount according to different RFID tags. The RFID tag 1 is installed within 5 minutes after the first adhesive 3 is coated. The RFID tag 1 is vertically placed by aligning a center of the RFID tag 1 with a center of the first adhesive 3, and is pressed in the direction as indicated by an arrow, so that the first adhesive 3 at the bottom overflows at the periphery of the tag.

Optionally, the surgical instrument installed with the RFID tag is cured for the first time, and placed in the indoor, for example, having a temperature in a range of 20-35° C., a humidity ≥30%, and the curing time may be 12 hours.

Optionally, the second adhesive is coated to the surface of the tag within 48 hours after the first adhesive is cured. After coating, it is required to shaping the second adhesive by evenly coating the portions of surface of the RFID tag not in contact with the second adhesive by using a tool such as a tweezers. The second adhesive must completely cover the surface and periphery of the tag and be evenly coated on the portions thereof, having a better appearance.

Optionally, after the second adhesive is shaped, the surgical instrument is baked to be cured. The surgical instrument is placed into an oven, and the surface of the second adhesive needs to be placed horizontally and upwardly, for example, the baking is set at 120° C. for 2 hours, and then the surgical instrument is taken out for cooling at an indoor temperature.

Optionally, after cooling, it is required to check whether the second adhesive completely covers the tag and whether there is a poor appearance such as air bubbles. If there is bubbles with diameter small than 0.5 mm, and no tag exposed, it is a normal phenomenon during the curing of the second adhesive. If such standard is not reached, it is required to disassemble the RFID tag and surgical instrument, clean up the residue of the adhesive, and then repeat the above-described steps.

For example, the specific disassembling steps are presented as follows: disassembling the adhesive and the RFID tag by using a diagonal pliers, in which the pliers should clamp the adhesive and the RFID tag to pull away from the surgical instrument body, so as to avoid damaging the surgical instrument; scraping the adhesive left over the surgical instrument by using a blade, in which the blade and the surgical instrument are kept as horizontal as possible so as to avoid scratching the surgical instrument; wiping the surface by using the alcohol after the adhesive is completely removed, and re-installing the RFID tag in the original position according to the process.

In one illustrative embodiment as provided in the present disclosure, the first adhesive is a silane adhesive, for example, is stored at an indoor sealing temperature of 5-30° C. In the same or different illustrative embodiments as provided in the present disclosure, the second adhesive is an epoxy-based adhesive, for example, is stored at a refrigerator sealing temperature <4° C., wherein the second adhesive is taken out before being used, and needs 2 hours and more to be warmed at an environmental temperature of 23-30° C.

For example, an adhesive applying device may include an air compressor and a pneumatic dispenser. The air compressor may be connected with the pneumatic and semi-automatic dispenser through an air tube. The pneumatic dispenser may be connected to an adhesive syringe through a dispensing air outlet pipe, wherein the adhesive syringe, for example, may have a needlestick with a diameter of 1 mm.

An installing method of a RFID tag used for a surgical instrument as provided in the first embodiment of the present disclosure includes sticking the RFID tag to the surgical instrument body by using the first adhesive, which may provide a firm installation strength; performing a first-time curing procedure with regard to the characteristics of the first adhesive, and covering and protecting the RFID tag by using the second adhesive, and a second-time curing procedure may be performed with regard to the characteristics of the adhesive, which may provide greater reliability and safety, and in line with medical safety standards. And, the installing method is convenient, and thereby it is convenient to be reworked whenever shortcomings occur, and the surgical instrument itself will not be damaged.

The Second Embodiment

Figure 4:
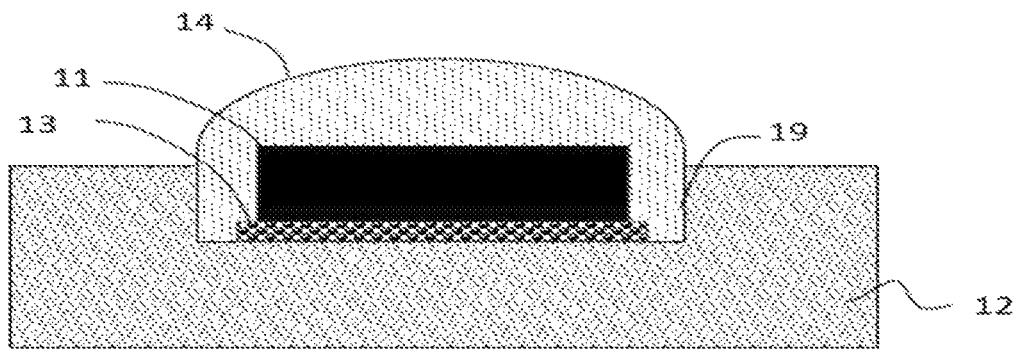
FIG. 4 is a schematic cross-sectional view of a RFID tag for a surgical instrument in an embodiment as provided by way of an example of the present disclosure.

Referring to FIG. 4, it shows a schematic view of the surgical instrument as provided by one implementation of the second embodiment of the present disclosure. As shown, the surgical instrument includes a surgical instrument body 12. A groove 19 is disposed on the surgical instrument body 12. A size of the groove 19 is slightly larger than a size of the RFID tag 11 installed on the surgical instrument body 12. A first adhesive 13 is disposed between the bottom surface of the RFID tag 11 and the groove 19. The first adhesive 13 firmly sticks the RFID tag 11 to the groove 19 of the surgical instrument together. A second adhesive 14 is disposed on the other surfaces of the RFID tag 11. The second adhesive 14 covers the RFID tag 11 and a part of surface of the surgical instrument body 12, and the second glue 14 is located within the groove 19.

The groove 19 is provided on the surgical instrument body 12, and the RFID tag 11 is adhered in the groove 19 by the first adhesive 13. The installation position of the RFID tag 11 is accurate so that problems such as displacement cannot arise due to external force such as touching when the first adhesive 13 is not cured. In addition, the groove 19 has a depth that generally cannot fully receive the RFID tag 11 therein, but may reduce the height of the RFID tag 11 exposed out of the surgical instrument body 12, so that the surgical instrument equipped with the RFID tag may be used more conveniently. In this embodiment of the present disclosure, the depth of the groove is less than the height of the RFID tag, because if the RFID tag is completely wrapped into the interior of the groove, a deep groove needs to be opened in the surgical instrument body, while the deep groove will be reduced its strength, and thereby affecting its service life, since the surgical instrument is a delicate instrument.

The second adhesive 14 is coated on the RFID tag 11, because the second adhesive 14 has certain flowability, and also needs to be shaped after the coating is finished, requesting its surface smooth, surfaces symmetric to each other and size unified. The surgical instrument as provided in the second embodiment of the present disclosure, due to existence of the groove 19, may arrange the second adhesive 14 within the groove 19, in order to control the coating area of the second adhesive 14, and thus the second adhesive can be shaped to have symmetric surfaces and unified size.

Figure 5:
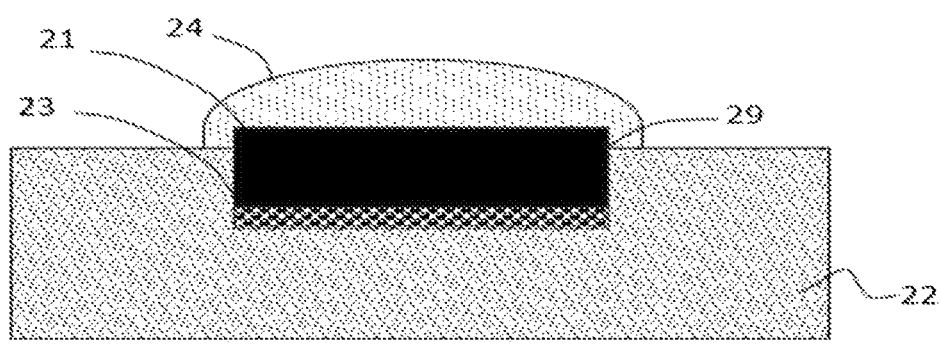
FIG. 5 is a schematic cross-sectional view of a RFID tag for a surgical instrument in an embodiment as provided by way of an example of the present disclosure.

Referring to FIG. 5, the second embodiment of the present disclosure further provides a further surgical instrument. As shown, the surgical instrument includes a surgical instrument body 22. A groove 29 is disposed on the surgical instrument body 12. A size of an opening of the groove 29 is matched with a size of the bottom of the RFID tag 21. A first adhesive 23 is disposed between the bottom surface of the RFID tag 21 and the groove 29. The first adhesive 23 firmly sticks the RFID tag 21 to the groove 29 of the surgical instrument together, and the RFID tag 21 is engaged in the groove 29.

The groove 29 is provided on the surgical instrument body 22, and the RFID tag 21 is adhered and engaged in the groove 29. The installation position of the RFID tag 21 is accurate so that problems such as displacement cannot arise due to external force such as touching when the first adhesive 23 is not cured. In addition, the groove 29 has a depth that generally cannot fully receive the RFID tag 21 therein, but may reduce the height of the RFID tag 21 exposed out of the surgical instrument body 22, so that the surgical instrument equipped with the RFID tag may be used more conveniently. Furthermore, the RFID tag 21 is fixed more firmly due to engagement of the groove 29. In this embodiment of the present disclosure, the depth of the groove is less than the height of the RFID tag. If the RFID tag is completely wrapped into the interior of the groove, a deep groove needs to be opened in the surgical instrument body, while the deep groove will be reduced its strength, and thereby affecting its service life, since the surgical instrument is a delicate instrument, A second adhesive 24 is coated on the RFID tag 21, and covers and protects the RFID tag 21, and side edges of the RFID tag 21 are adhered to the surgical instrument body 22 together. At a place where the RFID tag 21 is adhered to the surgical instrument body 22, the first adhesive 23 and the second adhesive 24 are not on the same plane, so that the RFID tag is adhered more securely.

Figure 6A:
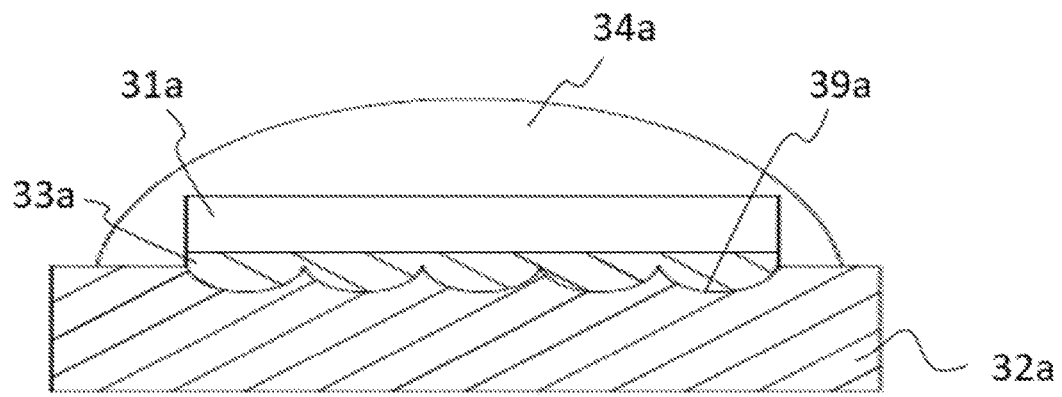
FIG. 6(a) is a schematic cross-sectional view of a RFID tag for a surgical instrument in an embodiment as provided by way of an example of the present disclosure.
Figure 6B:
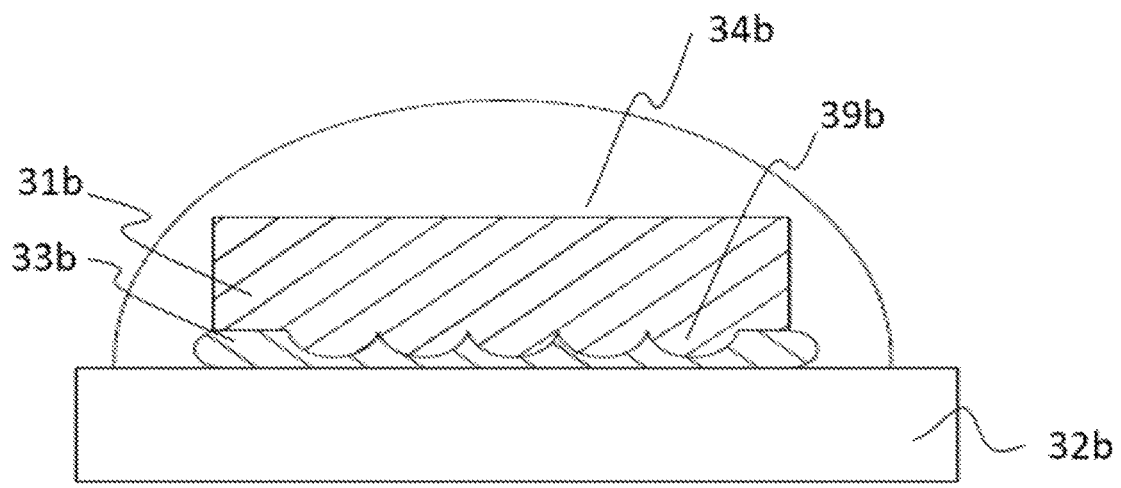
FIG. 6(b) is a schematic cross-sectional view of a RFID tag for a surgical instrument in an embodiment as provided by way of an example of the present disclosure.

Please referring to FIG. 6(a), a surgical instrument as provided by a further implementation of the second embodiment of the present disclosure, as shown, includes a surgical instrument body 32a. The surgical instrument body 32a is provided with a rough surface 39a. A first adhesive 33a is disposed between the bottom surface of the RFID tag 31a and the rough surface 39 of the surgical instrument body 32a. The first adhesive 33a adheres the RFID tag 31a to the rough surface 39a together. The rough surface 39a may be a polished surface or a surface provided with a plurality of shallow trenches. The rough surface 39a increases area for adhering to the first adhesive 33a, and thereby increasing a friction coefficient, such that the first adhesive 33a may adhere the RFID tag 31a to the surgical instrument body 32a more firmly. In other embodiments, the rough surface may also be provided on the bottom of the groove as shown in FIGS. 4 and 5. In FIG. 6(b), the bottom surface of the RFID tag 31b is designed as a rough surface, which may play a function of increasing the coating area of the first adhesive and increasing the friction coefficient, such that the adhesive intensity between the RFID tag 31b and the surgical instrument body 32b will be enhanced.

The second embodiment of the present disclosure also provides a method for installing a RFID tag on a surgical instrument, comprising the following steps of:

A. providing a surgical instrument body, on which surface treatment is performed;

B. cleaning the surface of the surgical instrument body;

C. providing a first adhesive to be coated on the treated surface of the surgical instrument body;

D. providing a RFID tag, and sticking the RFID tag on the first adhesive;

E. curing for a first time;

F. providing a second adhesive, and coating the second adhesive on the RFID tag and the surface of the surgical instrument body adjacent to the RFID tag;

G. curing for a second time.

Specifically, in one implementation, please referring to FIG. 4, in the step A, the surface treatment of the surgical instrument body is a grooving treatment, in which a groove 19 is formed on the surface of the surgical instrument body, and has a size slightly larger than the RFID tag 11 intended to be installed on the surgical instrument body 12. In the step C, the first adhesive 13 is coated on the bottom of the groove 19. In the step F, the second adhesive 14 is coated within the groove 19.

In another implementation, please referring to FIG. 5, in the step A, the surface treatment of the surgical instrument body is a grooving treatment, in which a groove 29 is formed on the surface of the surgical instrument body, and has an opening with a size that is matched with the size of the bottom of the RFID tag 21 intended to be installed on the surgical instrument body 22. In the step C, the first adhesive 23 is coated on the bottom of the groove 29. In the step D, the RFID tag 21 is engaged in the groove 29 while the RFID tag 21 is adhered onto the first adhesive 23.

In a further implementation, please referring to FIG. 6(a), in the step A, the surface treatment of the surgical instrument body 32 is a roughing or shallow-trenching treatment, so that the surface of the surgical instrument body 32 is roughened. In the step C, coating the first adhesive at the treated surface of the surgical instrument body 32 is coating the first adhesive 33 at the rough surface.

As for the surgical instrument as provided by the second embodiment of the present disclosure, the RFID tag may be installed on the surgical instrument more firmly, and precision and service life of the surgical instrument body are not damaged. The second embodiment of the present disclosure further provides a corresponding installing method, which is convenient for installation and operation.

The First Embodiment

Figure 7:
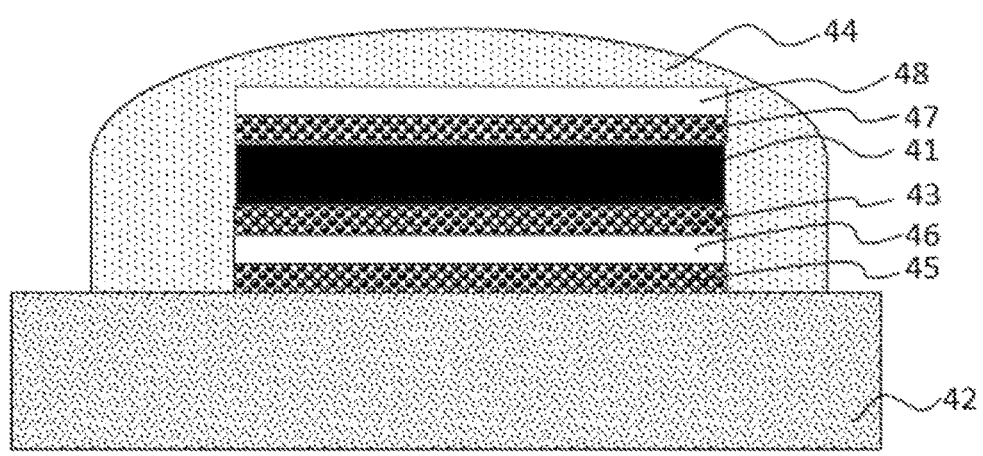
FIG. 7 is a schematic cross-sectional view of a RFID tag for a surgical instrument in an embodiment as provided by way of an example of the present disclosure.

Please referring to FIG. 7, it shows a schematic view of a surgical instrument as provided by the third embodiment of the present disclosure. As shown, the surgical instrument includes a surgical instrument body 42, a third adhesive 45 coated on the surgical instrument body 42, a first metal layer 46 adhered onto the third adhesive 45, a first adhesive 43 coated on the first metal layer 46, and a RFID tag 41 adhered onto the first adhesive 43. The surgical instrument further includes a fourth adhesive 47 coated on the RFID tag 41, a second metal layer 48 adhered onto the fourth adhesive 47, and a second adhesive 44 covering the second metal layer 48 to the third adhesive 45.

The RFID tag 41 may be a ceramic tag. A base of the RFID tag 41 is a plate-like ceramic block, on the surface of which an antenna coating layer is provided. When the ceramic tag is installed on the surface of the surgical instrument, different surgical instruments have different metal materials and shapes, which affect a reading distance and working frequency of the tag, particularly, when the same RFID tag is installed on different surgical instruments, there will be greater difference occurred in the reading distance or working frequency. With the above-described structure, the first metal layer 46 is adhered between the RFID tag 41 and the surgical instrument body 42, and the first metal layer 46 is isolated from the surgical instrument body 42 by the third adhesive 45, corresponding to that the RFID tag 41 is isolated by the first metal layer 46 from contacting the surface of the surgical instrument body 42, such that the influence of the surgical instrument body 42 on the performance of the RFID tag 41 can be reduced, and consistency of the performance of the RFID tag 41 installed on the different surgical instrument bodies 42 can be improved.

The second metal layer 48 is disposed on the upper side of the RFID tag 41 and is insulatively adhered by the fourth adhesive 47, corresponding to adding a suspended loading plate to the RFID tag 41, and the second metal layer 48 is not directly connected to the RFID tag 41, to constitute a passive vibrator loaded on the RFID tag 41, to improve the gain of the antenna of the RFID tag 41, increase the reading/writing distance of the antenna of the RFID tag 41, and expand the antenna bandwidth.

In the third embodiment, the function of the third adhesive and the fourth adhesive is to provide a stronger adhesive intensity to adhere the first metal, the second metal, and the surface of the RFID tag or the surface of the surgical instrument body together. The material of the third adhesive and the fourth adhesive may be selected as same as the material of the first adhesive.

In the third embodiment, the first metal layer and the second metal layer are added. In other embodiments, only the first metal layer or only the second metal layer may be provided.

The third embodiment of the present disclosure further provides a method for installing a RFID tag on a surgical instrument body, including the following steps of:

A. providing a surgical instrument body, and cleaning the surface of the surgical instrument body;

B. providing a third adhesive, and coating the third adhesive on the surface of the surgical instrument body;

C. providing a first metal layer, and sticking the first metal layer onto the third adhesive;

D. curing for a first time for curing the third adhesive;

E. providing a first adhesive, and coating the first adhesive on the first metal layer;

F. providing a RFID tag, and sticking the RFID tag to the first adhesive;

G. curing for a second time for curing the first adhesive;

H. providing a fourth adhesive, and coating the fourth adhesive on the RFID tag;

I. providing a second metal layer, and sticking the second metal layer to the RFID tag;

J. curing for a third time for curing the fourth adhesive;

K. providing a second adhesive, and coating the second adhesive on the RFID tag and the surface of the surgical instrument body adjacent to the RFID tag;

L. curing for a fourth time for curing the second adhesive.

The surgical instrument and the installing method as provided by the third embodiment of the present disclosure securely fixes the RFID tag on the surgical instrument body and also optimize performance of the RFID tag itself to play a better effect when the RFID tag is used on the surgical instrument.

As compared with the prior art, the method for installing the tag in one embodiment of the present disclosure may be adapted to surgical instruments of various sizes and surface shapes. As long as the tag with matched size is selected, the tag may be firmly attached to a surface of the instrument without falling off, and performance of the tag itself cannot be affected, such that operation of medical personnel during use cannot be affected and an excellent reading effect can be achieved. The tag according to one embodiment of the present disclosure may be in line with the medical standards and biocompatibility, and can withstand repeated steam sterilization at a higher temperature and high pressure and chemical cleaning cycles. In one embodiment of the present disclosure, the size and the installing way of the tag itself are more flexible, and thereby being adaptive to special volumetric shape of the surgical instruments, to overcome inconvenience for the doctor in clinical operation brought by the surgical instrument to which the tag is installed by the way of welding, and to be used under a metal environment.

The present disclosure has been described through some preferable embodiments as above described. It is apparent that those skilled in the art can make modifications and variations to the invention without departing from the scope of the invention. The present disclosure is intended to cover the modifications and variations provided that they fall in the scope of protection defined by the following claims or their equivalents.

What is claimed is:

1. A surgical instrument, comprising a surgical instrument body, a RFID tag and an adhesive, the surgical instrument body and the RFID tag are fixedly connected as a whole by the adhesive, wherein the adhesive comprises a first adhesive and a second adhesive;

the first adhesive is disposed between a bottom surface of the RFID tag and a surface of the surgical instrument body, the other surfaces of the RFID tag are covered by the second adhesive, the second adhesive also covers an intersection of the RFID tag with the surgical instrument body; and the first adhesive and the second adhesive are different types of adhesives, and an adhesive intensity of the first adhesive is greater than an adhesive intensity of the second adhesive, and fluidity of the second adhesive is greater than fluidity of the first adhesive.

2. The surgical instrument according to claim 1, wherein a groove is disposed on the surgical instrument body, the RFID tag and a face of the adhesive in contact with the surgical instrument body are within the groove.

3. The surgical instrument according to claim 1, wherein a groove is disposed on the surgical instrument body, a size of an opening of the groove is matched with a size of the bottom of the RFID tag, and the RFID tag is engaged in the groove.

4. The surgical instrument according to claim 1, wherein the first adhesive is selected from any one of a silane adhesive and an organic silicone adhesive; and the second adhesive is an epoxy adhesive.

5. The surgical instrument according to claim 1, wherein a portion of the surgical instrument body adhered to the bottom surface of the RFID tag is a rough surface.

6. The surgical instrument according to claim 1, wherein a portion of the bottom surface of the RFID tag adhered to the surgical instrument body is a rough surface.

7. The surgical instrument according to claim 1, wherein the first adhesive is a conductive adhesive.

8. The surgical instrument according to claim 1, wherein the surgical instrument further comprises a first metal layer disposed between the surgical instrument body and the bottom surface of the RFID tag, the first metal layer is adhered to the surgical instrument body by a third adhesive, and the first metal layer is further adhered to the bottom surface of the RFID tag by a fourth adhesive.

9. The surgical instrument according to claim 8, wherein a material of the third adhesive is identical to a material of the first adhesive.

10. The surgical instrument according to claim 1, wherein the surgical instrument further comprises a second metal layer disposed on a top of the RFID tag, the second metal layer is adhered to the top of the RFID tag by a fourth adhesive, and the second adhesive covers the second metal layer and the RFID tag.

11. The surgical instrument according to claim 10, wherein a material of the fourth adhesive is identical to the material of the first adhesive.

* * * * *